(12) United States Patent
Bianchi et al.

(10) Patent No.: US 7,572,827 B2
(45) Date of Patent: Aug. 11, 2009

(54) USE OF ANGELICIN AND OF ITS STRUCTURAL ANALOGUES FOR THE TREATMENT OF THALASSEMIA

(75) Inventors: Nicoletta Bianchi, Mezzogoro (IT); Monica Borgatti, Ferrara (IT); Roberto Gambari, Bologna (IT); Ilaria Lampronti, Ferrara (IT)

(73) Assignees: Universita' Degli Studi Di Ferrara, Ferrara (IT); Associazione Veneta Per La Lotta Alla Talassemia, Rovigo (IT)

( * ) Notice: Subject to any disclaimer, the term of this patent is extended or adjusted under 35 U.S.C. 154(b) by 409 days.

(21) Appl. No.: 10/522,737

(22) PCT Filed: Jul. 30, 2003

(86) PCT No.: PCT/IB03/03462

§ 371 (c)(1),
(2), (4) Date: Oct. 12, 2005

(87) PCT Pub. No.: WO2004/012729

PCT Pub. Date: Feb. 12, 2004

(65) Prior Publication Data

US 2006/0111433 A1    May 25, 2006

(30) Foreign Application Priority Data

Jul. 31, 2002   (IT) .............................. TO02A0684

(51) Int. Cl.
*A61K 31/366* (2006.01)
(52) U.S. Cl. ..................................... 514/453
(58) Field of Classification Search ............ None
See application file for complete search history.

(56) References Cited

U.S. PATENT DOCUMENTS

| | | |
|---|---|---|
| 4,021,559 A | 5/1977 | Giudiceli et al. |
| 5,569,675 A | 10/1996 | Rephaeili et al. |

FOREIGN PATENT DOCUMENTS

| | | | |
|---|---|---|---|
| JP | 08231417 A | * | 9/1996 |
| WO | WO 96 23495 A | | 8/1996 |
| WO | WO 96 40271 A | | 12/1996 |

OTHER PUBLICATIONS

Lampronti et al., European Journal of Haematology, 2003, 71(3), 189-195.*
X S Xu et al.: "Activation of Human Gamma-Globin Gene Expression via Triplex-forming Oligonucleotide (TFO)-directed mutations in the gamma-globin gene 5' flanking region" GENE. Netherlands Jan. 25, 2000, vol. 242, No. 1-2, pp. 219-228, XP002260187, ISSN: 0378-1119.
Iiara et Lampronti et al: "Accumulation of gamma-globin mRNA in human erythroid cells treated with angelicin." European Journal of Haematology, Denmark, Sep. 2003, vol. 71, No. 3, pp. 189-195, XP002260188, ISSN: 0902-4441.
D Rund et al.: "Pathophysiology of Alpha and Beta-Thalassemia: Therapeutic Implications" Seminars in Hematology, Philadelphia, PA, US, vol. 38, No. 4, Oct. 2001, p. s343-349, XP008015321, ISSN: 0037-1963.
MERK: "The Merk Index" 1999, Merk Research Laboratories, USA, XP002260189, p. 881, col. 1—p. 883, col. 2.
E.A. Rachmilewitz, et al., "Novel Treatment Options in the Severe β-Globin Disorders," *British Journal of Haematology*, 1995, vol. 91, pp. 263-268.
J. Rochette, et al., "Fetal Hemoglobin Levels in Adults," *Blood Reviews*, 1994, vol. 8, pp. 213-224.
Nicoletta Bianchi, et al., "Accumulation of γ-globin mRNA and induction of erythroid differentiation after treatment of human leukaemic K562 cells with tallimustine," *British Journal of Haematology*, 2001, vol. 113, pp. 951-961.
George J. Dover, et al., "Increased Fetal Hemoglobin in Patients Receiving Sodium 4-phenylbutyrate," *The New England Journal of Medicine*, vol. 327, No. 8, pp. 569-570, Aug. 20, 1992.
Tohru Ikuta, et al., "Cellular and Molecular Effects of a Pulse Butyrate Regimen and New Inducers of Globin Gene Expression and Hematopoiesis," *Annals New York Academy of Sciences*, pp. 87-99, vol. 850, 1998.
Ling Dong Kong, et al., "Inhibition of Rat Brain Monoamine Oxidase Activities by Psoralen and Isopsoralen: Implications for the Treatment of Affective Disorders," *Pharmacology & Toxicology*, 2001, vol. 88, pp. 75-80.
Luisa Mosti, et al., "Synthesis of angelicin heteranalogues: preliminary photobiological and pharmacological studies," *Il Farmaco*, vol. 53, 1998, pp. 602-610.
Soroush Sardari, et al., "Synthesis and Antifungal Activity of Coumarins and Angular Furanocoumarins," *Bioorganic & Medicinal Chemistry*, vol. 7, 1999, pp. 1933-1940.
Andreas E. Jakobs, et al., "A Convenient Synthesis of Thiopyrano [2,3-*e*]benzofuran: A New Sulfur Analogue of Angelicin," *J. Org. Chem.*, 1996, vol. 61, pp. 4842-4844.
Marzia Iester, et al., "Synthesis and Photobiological Properties of 3-acylangelicins, 3-alkoxycarbonylangelicins and Related Derivatives," *Il Farmaco*, vol. 50, No. 10, pp. 669-678, 1995.
Emile Bisagni, et al., "Synthesis of psoralens and analogues," *J. Photochem. Photobiol. B: Biol.*, vol. 14, 1992, pp. 23-46.
Francesco Dall'Acqua, et al., "4'-Methylangelicins: New Potential Agents for the Photochemotherapy of Psoriasis," *J. Med. Chem.*, 1983, vol. 26, pp. 870-876.

(Continued)

*Primary Examiner*—Brian-Yong S Kwon
(74) *Attorney, Agent, or Firm*—Sughrue Mion, PLLC

(57) ABSTRACT

The use of angelicin and its structural analogues for the preparation of a medicament for the therapeutic treatment of beta-thalassaemia is described. A structural analogue which is particularly preferred for this purpose is bergapten.

2 Claims, No Drawings

OTHER PUBLICATIONS

Francesco Dall'Acqua, et al., "Methylangelicins: New Potential Agents for the Photochemotherapy of Psoriasis. Structure-Activity Study on the Dark and Photochemical Interactions with DNA," *J. Med. Chem.*, 1981, vol. 24, pp. 806-811.

Maria Teresa Conconi, et al., "Antiproliferative Activity and Phototoxicity of some Methyl Derivatives of 5-Methoxpsoralen and 5-Methoxyangelicin," *Pharmacology & Toxicology*, 1998, vol. 82, pp. 193-198.

C. Marzano, et al., "DNA Damage and Cytotoxicity Induced in Mammalian Cells by a Tetramethylfuroquinolinone Derivative," *Environmental and Molecular Mutagenesis*, vol. 29, pp. 256-264, 1997.

Franco Bordin, et al., "Angelicins, Angular Analogs of Psoralens: Chemistry, Photchemical, Photobiological and Phototherapeutic Properties," *Pharmac. Ther.*, vol. 52, pp. 331-363, 1991.

C. Nadine Backhouse, et al., "Active constituents isolated from *Psoralea glandulosa* L. with anti-inflammatory and antipyretic activities," *Journal of Enthopharmacology*, vol. 78, 2001, pp. 27-31.

Nicoletta Bianchi, et al., "Induction of Erythroid Differentiation of Human K562 Cells by Cisplatin Analogs," *Biochemical Pharmacology*, vol. 60, pp. 31-40, 2000.

Nicoletta Bianchi, et al., "The DNA-binding drugs mithramycin and chromomycin are powerful inducers of erythroid differentiation of human K562 cells," *British Journal of Haematology*, 1999, vol. 104, pp. 258-265.

E. Fibach, "Techniques for Studying Stimulation of Fetal Hemoglobin Production in Human Erythroid Cultures," *Hemoglobin*, vol. 22, Nos. 5&6, pp. 445-458, 1998.

Eitan Fibach, et al., "Hydroxyurea Increases Fetal Hemoglobin in Cultured Erythroid Cells Derived From Normal Individuals and Patients With Sickle Cell Anemia or β-Thalassemia," *Blood*, Vo. 81, No. 6, pp. 1630-1635, Mar. 15, 1993.

Christian A. Heid, et al., "Real Time Quantitative PCR," *Genome Research*, vol. 6, pp. 986-994, 1996.

Ursula E.M. Gibson, et al., "A Novel Method for Real Time Quantitative RT-PCR," *Genome Research*, vol. 6, pp. 995-1001, 1996.

* cited by examiner

SEQUENCE LISTING

<160> NUMBER OF SEQ ID NOS: 3

<210> SEQ ID NO 1
<211> LENGTH: 21
<212> TYPE: DNA
<213> ORGANISM: artificial
<220> FEATURE:
<223> OTHER INFORMATION: primer

<400> SEQUENCE: 1
tggcaagaag gtgctgactt c                   21

<210> SEQ ID NO 2
<211> LENGTH: 19
<212> TYPE: DNA
<213> ORGANISM: artificial
<220> FEATURE:
<223> OTHER INFORMATION: primer

<400> SEQUENCE: 2
tcactcagct gggcaaagg                      19

<210> SEQ ID NO 3
<211> LENGTH: 24
<212> TYPE: DNA
<213> ORGANISM: artificial

-continued

```
<220> FEATURE:
<223> OTHER INFORMATION: gamma-globin probe

<400> SEQUENCE: 3
tgggagatgc cataaagcac ctgg                                          24
```

USE OF ANGELICIN AND OF ITS STRUCTURAL ANALOGUES FOR THE TREATMENT OF THALASSEMIA

This is a National Stage entry of International Application PCT/IB2003/003462, with an international filing date of Jul. 30, 2003, which was published under PCT Article 21(2) as WO 2004/012729 A1, and the complete disclosure of which is incorporated into this application by reference.

The present invention relates to a novel therapeutic use of angelicin and its structural analogues as molecules capable of inducing erythroid cell differentiation and of increasing the production of gamma-globin mRNA.

The existence of substances capable of inducing the expression of the gamma-globin gene and the biosynthesis of foetal haemoglobin (HbF) in adult subjects has been known for some time (1). In the majority of cases, those substances are also capable of activating or potentiating the transcription of genes for embryonic and foetal globins in experimental model systems.

Recently, for example, numerous DNA-binding molecules have been described that have the capacity to bring about an increase in the expression of genes for gamma-globin (2). Among these there may be mentioned cisplatin and analogues of cisplatin, mithramycin, chromomycin, and tallimustine (3). Such molecules are efficient modulators of the expression of gamma-globin genes.

In human beings, activation of the transcription of genes for gamma-globins in adult subjects leads to the production of foetal haemoglobin mimicking the phenotype HPFH (High Persistence of Foetal Haemoglobin) which confers a favourable clinical picture on patients suffering from beta-thalassaemia also in homozygotic form (4). A therapy providing for the use of molecules having such activity for the treatment of patients suffering from beta-thalassaemia could therefore make those subjects less dependent on transfusion therapy (5).

The present invention is based on the need for novel modifiers of the transcription process which can be used in the treatment of beta-thalassaemia and which have a high level of induction of the expression of gamma-globin genes and at the same time a lower cytotoxic effect than reference drugs.

We have surprisingly found that angelicin—an isopsoralen derivative which has photochemotherapic activity—as well as its structural analogues, possesses such activity. In particular, it has been found that angelicin and its structural analogues are capable of potentiating the expression of the gene for human gamma-globin.

This activity is unexpected in the light of the known therapeutic uses of angelicin and of its structural analogues (6-18).

Angelicin has in fact been proposed in the literature for the treatment of psoriasis (12, 13), as an antiproliferative agent (14, 15, 16), as an antifungal agent (8), and as an anti-inflammatory agent (17).

The structural formula of angelicin is as follows:

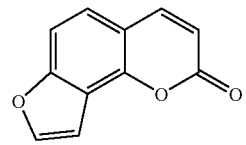

Angelicin (2-oxo-(2H)-furo-(2,3-h)-1-benzopyran)

The chemical synthesis of angelicin and its structural analogues has been described in the literature (see, for example, references 6-11).

Structural analogues of angelicin are, for example, linear and angular coumarins, optionally substituted, heteroanalogues of angelicin, thiopyrano-benzofurans, acylangelicins, alkylangelicins, alkoxycarbamoylangelicins, psoralens and isopsoralens, optionally substituted. A specific example is the linear furanocoumarin analogue bergapten (5-methoxypsoralen) which is currently used in PUVA (Psoralens plus UVA radiation) therapy for the treatment of psoriasis.

The structural formula of bergapten is as follows:

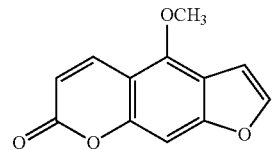

Bergapten (5-methoxypsoralen)

By virtue of their capacity to potentiate the expression of the gene for human gamma-globin, angelicin and its structural analogues can advantageously be used for the therapeutic treatment of patients suffering from beta-thalassaemia.

A first subject of the present invention is therefore the use of angelicin or a structural analogue thereof for the preparation of a medicament for the therapeutic treatment of beta-thalassaemia.

The structural analogue is preferably selected from the group consisting of linear and angular coumarins, optionally substituted, heteroanalogues of angelicin, thiopyrano-benzofurans, acylangelicins, alkylangelicins, alkoxycarbamoylangelicins, psoralens, and isopsoralens, optionally substituted.

A particularly preferred structural analogue is bergapten.

Moreover, as has been recently described (18, 19), a combined treatment with various modifiers of the transcription process permits a further increase in the expression of genes for gamma-globin.

Therefore, a second subject of the present invention is the use of angelicin or a structural analogue thereof in combination with at least one further modifier of the transcription process for the preparation of a medicament for the treatment of beta-thalassaemia.

According to a preferred embodiment, the further modifier of the transcription process is selected from the group consisting of cytosine arabinoside, retinoic acid, plicamycin, hydroxyurea, guanine, guanosine triphosphate (GTP), guanosine diphosphate (GDP) and guanosine monophosphate (GMP). Of these, cytosine arabinoside and retinoic acid are more preferred.

The activity of angelicin as an inducer of erythroid cell differentiation and the production of gamma-globin mRNA has been evaluated in human cell cultures.

The results of this study are illustrated in the following Examples. The data given in the Examples indicate that the activity of angelicin is greater than that of hydroxyurea which is a reference drug for the induction of foetal haemoglobin (HbF). It has also been ascertained that the cytotoxic effect which may be encountered is much lower than that of hydroxyurea.

The Examples which follow are provided for the purposes of illustration and are not intended to limit the scope of the invention in any way.

EXAMPLE 1

The biological activity of angelicin was evaluated by examining the capacity of that compound to modulate the expression of genes for gamma-globin in the human cell line K562, which is capable of differentiating in the erythroid manner by expressing genes for gamma-globin if subjected to treatment with modifiers of the biological response that are suitable for the purpose (3, 18, 19).

The level of differentiation was evaluated by analyzing the positive reaction of the cells to benzidine (3). The production of haemoglobin was evaluated by electrophoresis on cellulose acetate and by colouring the gel with a solution based on benzidine/$H_2O_2$ (3). The expression of the genes encoding for gamma-globin was evaluated by quantitative RT-PCR (reverse transcriptase PCR) (3).

Some of the data obtained are given in Table 1. As will be readily appreciated, angelicin (400 μM) is capable of bringing about an increase in the percentage of K562 cells that react positively to benzidine (55-60% of the cells treated, compared with 3-4% of the control K562 cells). The chief haemoglobin produced by K562 cells treated with angelicin was Hb Portland (alpha2gamma2). The data obtained by quantitative RT-PCR demonstrate that this effect on differentiation is associated with an increase in the intracytoplasmic accumulation of mRNA for gamma-globin. These evaluations were carried out after induction with 400 μM angelicin for 6 days.

Bergapten also showed the capability to bring about differentiation (measured as increase in cells that react positively to benzidine), although this capability was associated with a lesser increase in the accumulation of mRNA for globin.

The induction of erythroid differentiation in cells treated with angelicin is very similar to that obtained with cytosine arabinoside, which is one of the most effective known inducers (18, 19). However, the activity of angelicin on the increase in production of mRNA for gammma-globin is significantly greater than that of cytosine arabinoside.

TABLE 1

| Compound | Concentration (μM) | [a]Erythroid differentiation (%) | [b]Gamma-globin mRNA |
|---|---|---|---|
| — | — | 3-4 | 1 |
| cytosine arabinoside | 1 | 75-80 | 3.24 |
| bergapten | 200 | 50-60 | 3.48 |
| angelicin | 400 | 55-60 | 44.94 |

[a]Erythroid differentiation = percentage of K562 cells that react positively to benzidine (mean ± SD of six experiments). The concentrations indicated are those that are optimal for each molecule in order to activate the erythroid differentiation. Increasing these concentrations brings about a reduction in the effect on the differentiation parameters in combination with a cytotoxic activity of the molecules themselves.
[b]The accumulation of RNA for gamma-globin is given in the Table as an increase compared with that of untreated control K562 cells. The technique used was that of quantitative RT-PCR (22, 23) using the following primer and probe oligonucleotides: gamma-globin forward primer, 5'-TGG CAA GAA GGT GCT GAC TTC-3' (SEQ ID NO: 1); gamma-globin reverse primer, 5'-TCA CTC AGC TGG GCA AAG G-3' (SEQ ID NO: 2); gamma-globin probe 5'-FAM-TGG GAG ATG CCA TAA AGC ACC TGG-TAMRA-3' (FAM = 6-carboxy fluorescein, TAMRA = 6-carboxy-N,N,N',N'-tetramethyl-rhodamine) (SEQ ID NO: 3). The analyses were carried out on material extracted from cells treated for 6 days in the conditions indicated.

EXAMPLE 2

In order to check whether angelicin was also capable of stimulating the production of mRNA for gamma-globin in human erythroid precursors isolated from peripheral blood, the technique published by Fibach et al. (20, 21) was used. This technique provides for two stages: in the first stage, the cells isolated from peripheral blood of a subject who is healthy or suffering from a haemopoietic pathology, such as sickle cell anaemia or beta-thalassaemia, are sown in a culture medium to which 10% of conditioned medium derived from the vesicle carcinoma cell line 5637 has been added. The second stage consists in cultivating the isolated cells in a suitable culture medium, supplemented by the erythropoietin hormone, 30% bovine foetal serum, 2-mercaptoethanol, albumin, glutamine and desamethasone in order to permit the proliferation and maturing of stem cells of the erythroid type. In this stage the cells can be treated with potential HbF inducers. For example, with this system it was demonstrated that hydroxyurea, an inhibitor of DNA synthesis currently used in the experimental therapy of beta-thalassaemia, is capable of bringing about the production of HbF.

The results obtained by this technique demonstrated an increase in the production of mRNA for gamma-globin in cells treated with angelicin compared with the same untreated cells (20.53 times). This increase is greater than that which may be encountered using hydroxyurea (Table 2).

TABLE 2

| Compound | Concentration (μM) | [a]Gamma-globin mRNA |
|---|---|---|
| — | — | 1 |
| angelicin | 500 | 20.53 |
| hydroxyurea | 120 | 6.96 |

[a]The accumulation of RNA for gamma-globin is given in the Table as an increase compared with that of untreated control erythroid precursors. The technique used was that of quantitative RT-PCR (22, 23) using the primer and probe oligonucleotides described in Table 1. The hydroxyurea was used at a concentration of 120 μM since this molecule has a high cytotoxic activity at concentrations comparable with those used for angelicin. This highly cytotoxic activity starts to be encountered at concentrations greater than 250-300 μM.

BIBLIOGRAPHY

1. Rodgers G P, Rachmilewitz E A, British J. Haematology, 91:263-268, 1995.
2. Rochette J, Craig J E and Thein S L, Blood Reviews, 8: 213-224, 1994.
3. Bianchi N, Chiarabelli C, Borgatti M, Mischiati C, Fibach E, Gambari R. Br. J. Haematol, 113(4):951-61, 2001.
4. Dover G J, Brusilow S, Samid D, New England Journal of Medicine, 327: 569-570, 1992.
5. Ikuta T, Atweh G, Boosalis V, White G L, De Fonseca S, Boosalis M, Faller D V, Perrine S P, Annals of New York Academy of Sciences, 850:87-99, 1998.
6. Kong L D, Tan R X, Woo A Y, Cheng C H. Pharmacol Toxicol, 88(2):75-80, 2001.
7. Mosti L, Lo Presti E, Menozzi G, Marzano C, Baccichetti F, Falcone G, Filippelli W, Piucci B. Il Farmaco, 53(8-9): 602-10, 1998.
8. Sardari S, Mori Y, Horita K, Micetich R G, Nishibe S, Daneshtalab M. Bioorg Med Chem, 7(9):1933-40, 1999.
9. Jakobs A E, Christiaens L. J Org Chem, 61(14):4842-4844, 1996.
10. Iester M, Fossa P, Menozzi G, Mosti L, Braccichetti F, Marzano C, Simonato M. Il Farmaco, 50 (10): 669-678, 1995.
11. Bisagni E. Photochem Photobiol, Review, 14(1-2):23-46, 1992.
12. Dall'Acqua F, Vedaldi D, Bordin F, Baccichetti F, Carlassare F, Tamaro M, Rodighiero P, Pastorini G, Guiotto A, Recchia G, Cristofolini. J Med Chem, 26(6):870-6, 1983.
13. Dall'Acqua F, Vedaldi D, Guiotto A, Rodighiero P, Carlassare F, Baccichetti F, Bordin F. J Med Chem, 24(7):806-11, 1981.
14. Conconi M T, Montesi F, Parnigotto P P. Pharmacol Toxicol, 82(4):193-8, 1998.
15. Marzano C, Severin E, Pani B, Guiotto A, Bordin F. Environ Mol Mutagen, 29(3):256-64, 1997.
16. Bordin F, Dall'Acqua F, Guiotto A. Pharmacol Ther, Review, 52(3):331-63, 1991.
17. Backhouse C N, Delporte C L, Negrete R E, Erazo S, Zuniga A, Pinto A, Cassels B K. J. Ethnopharmacol, 78(1): 27-31, 2001.
18. Bianchi N, Ongaro F, Chiarabelli C, Gualandi L, Mischiati C, Bergamini P, Gambari R. Biochem Pharmacol, 60:31-40, 2000.
19. Bianchi N, Osti F, Rutigliano C, Ginanni Corradini F, Borsetti E, Tomassetti M, Mischiati C, Feriotto G and Gambari R, British Journal of Haematology, 104:258-263, 1999.
20. Fibach E. Hemoglobin, 22: 445-458, 1998.
21. Fibach E, Burke K P, Schechter A N, Noguchi C T & Rodgers G P. Blood, 81: 1630-1635, 1993.
22. Heid C A, Stevens J, Livak K J & Williams P M. Genome Research, 6: 986-994, 1996.
23. Gibson U E, Heid C A & Williams P M. Genome Research, 6: 995-1001, 1996.

What is claimed is:

1. A method for treating beta-thalassaemia, comprising administering to a subject in need of treatment an effective amount of angelicin, represented by formula (1):

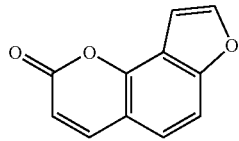

or a structural analogue thereof,
wherein the structural analogue is selected from the group consisting of an acylangelicin, an alkylangelicin, an alkoxycarbamoylangelicin and bergapten.

2. The method according to claim 1, wherein the angelicin or structural analogue is in combination with at least one further modifier of the transcription process, wherein the further modifier of the transcription process is selected from the group consisting of cytosine arabinoside, retinoic acid, plicamycin, mithramycin, hydroxyurea, guanine, guanosine triphosphate (GTP), guanosine diphosphate (GDOP) and guanosine monophosphate (GMP).

* * * * *